US008552391B2

(12) United States Patent
Terenetska et al.

(10) Patent No.: US 8,552,391 B2
(45) Date of Patent: Oct. 8, 2013

(54) METHODS AND DEVICES FOR IN SITU DETERMINATION OF A VITAMIN-D SYNTHESIZING AMOUNT OF NATURAL AND ARTIFICIAL UV IRRADIATION

(75) Inventors: Iryna P. Terenetska, Kiev (UA); Tetiana M. Orlova, Kiev (UA); Eugene K. Kirilenko, Kiev (UA); Grygory A Galich, Kiev (UA); Anna M. Eremneko, Kiev (UA)

(73) Assignee: Lawrence Livermore National Security, LLC., Livermore, CA (US)

( * ) Notice: Subject to any disclaimer, the term of this patent is extended or adjusted under 35 U.S.C. 154(b) by 138 days.

(21) Appl. No.: 13/148,804

(22) PCT Filed: Mar. 23, 2010

(86) PCT No.: PCT/US2010/028268
§ 371 (c)(1),
(2), (4) Date: Aug. 10, 2011

(87) PCT Pub. No.: WO2010/111241
PCT Pub. Date: Sep. 30, 2010

(65) Prior Publication Data
US 2011/0309249 A1  Dec. 22, 2011

(30) Foreign Application Priority Data
Mar. 24, 2009  (UA) .................................. 200902721

(51) Int. Cl.
*G01T 1/02* (2006.01)
*G03B 11/00* (2006.01)
(52) U.S. Cl.
USPC .................. 250/370.07; 250/482.1

(58) Field of Classification Search
USPC ...................................................... 250/370.07
See application file for complete search history.

(56) References Cited

U.S. PATENT DOCUMENTS

| 1,896,191 | A |   | 2/1933  | Zimmermann et al. |
| 5,472,954 | A | * | 12/1995 | Loftsson ......................... 514/58 |
| 5,777,735 | A | * | 7/1998  | Reagen .......................... 356/451 |
| 2005/0123735 | A1 | * | 6/2005 | Lu et al. ..................... 428/304.4 |
| 2010/0303804 | A1 | * | 12/2010 | Liska et al. ................. 424/130.1 |

FOREIGN PATENT DOCUMENTS

| UA | 15712 | 7/2006 |
| UA | 19525 | 12/2006 |

OTHER PUBLICATIONS

Terenetskaya, Irina, Spectral Monitoring of Biologically Active Solar UVB Radiation Using an in vitro Model of Vitamin D Synthesis, Oct. 2000, Talanta, vol. 53, Issue 1, pp. 195-203.*

Terenetskaya & Gvozdovskyy, An in situ Monitoring of Biologically Active Solar UV-B Radiation: A new Biosensor of Vitamin D Synthetic Capacity, 2001, Proceedings of SPIE, vol. 4425, pp. 183-188.*

(Continued)

*Primary Examiner* — David Porta
*Assistant Examiner* — Jeremy Valentiner
(74) *Attorney, Agent, or Firm* — Steinfl & Bruno, LLP (57) ABSTRACT

A matrix with a biologically active substance is exposed to UV radiation. The biologically active substance is selected to initiate photoconversions originating vitamin D synthesis. An optical parameter of the biologically active substance is being changed under UV irradiation. Change of the optical parameter is measured, thus measuring the amount of UV radiation that has caused the vitamin D synthesis occurred through photoconversion. Measuring occurs by way of a dosimeter.

21 Claims, 5 Drawing Sheets

(56) References Cited

OTHER PUBLICATIONS

KR 588332 B1 (Kim K H), Electronic Personal Radiation Dosimeter, for Reducing Weight and Volume and Accurately and Quickly Measuring Dose by Removing Noise, Aug. 2007, Derwent Publications Ltd., pp. 1-3.*

PCT International Search Report for PCT/US2010/028268 filed on Mar. 23, 2010 in the name of Lawrence Livermore National Security, LLC.

PCT Written Opinion mailed on Sep. 28, 2010 for PCT Application No. PCT/US2010/028268 filed Mar. 23, 2010 in the name of Lawrence Livermore National Security, LLC.

Holick, M., Vitamin D: A Millenium Perspective, J. Cell. Biochem. 2003, 88: 296-307.

Orlova, TN, et al., Possible use of provitamin d3 photoisomerization for spectral dosimetry of bioactive antirachitic uv radiation, J. Appl. Spectro. 2009, 76: 240-244.

Terenetskaya, IP, et al., An in situ monitoring of biologically active solar UV-B radiation: A new biosensor of vitamin D synthetic capacity, Proceedings of SPIE 2001, 4425: 183-188.

Terenetskaya, IP, Spectral monitoring of biologically active solar UVB radiation using an in vitro model of vitamin D synthesis, Talanta 2000, 53: 195-203.

Terenetskaya, IP, Limitations of the photostationary approximation in the photochemistry of provitamin d: the ambiguous role of the irreversible degradation channel, Theoretical & Exp. Chme. 2008, 44: 286-292.

Webb, AR et al., Influence of season and latitude on the cutaneous synthesis of vitamin D3: Exposure to winter sunlight in Boston and Edmonton will not promote Vitamin D3 synthesis in human skin, J. Clin. Endo. 1988, 67: 373-378.

\* cited by examiner

METHODS AND DEVICES FOR IN SITU DETERMINATION OF A VITAMIN-D SYNTHESIZING AMOUNT OF NATURAL AND ARTIFICIAL UV IRRADIATION

CROSS REFERENCE TO RELATED APPLICATIONS

The present application is the US national stage of International Application PCT/IB2010/028268 filed on Mar. 23, 2010 which, in turn, claims priority to Ukrainian Patent Application 200902721 filed on Mar. 24, 2009.

The present application claims priority to Ukraine patent application no. 2009 02721 filed on Mar. 24, 2009, entitled "A Method For Determination In Situ Of The Vitamin-D-Synthetic Dose Of Natural And Artificial Ultraviolet Irradiation And Personal Biodosimeter For Its Implementation" incorporated herein by reference in its entirety. The presented application may also be related to Ukraine patent no. 15712U which is also incorporated herein by reference in their entirety.

FIELD

The present disclosure relates to photobiology and photochemistry. More in particular, it relates to methods and devices for in situ determination of a vitamin-D synthesizing amount of natural and artificial UV irradiation.

BACKGROUND

Vitamin D is a fat-soluble prohormone that can be synthesized from initial provitamin D upon UV radiation (typically sun exposure).

However, biological activity of ultraviolet (UV) radiation can produce both positive (synthesis of vitamin D) and negative effects (erythema and skin aging, immune suppression, etc.).

Therefore, monitoring of acquired UV doses of ultraviolet radiation is desirable but can be challenging. In particular, detection in situ of UV doses of ultraviolet radiation, and/or detection of the vitamin-D-synthetic ability of UV radiation, can be challenging although the synthesis of vitamin $D_3$ in human skin is an important positive effect of ultraviolet irradiation.

SUMMARY

Provided herein are a biodosimeter, methods and systems that in several embodiments allow detection of UV absorption, and/or vitamin D synthetic ability of UV radiation. In particular, in several embodiments, biodosimeters, methods and systems herein described allow in situ detection of UV radiation and related vitamin D synthetic ability.

According to a first aspect, a method for determination in situ of vitamin-D synthesizing amount of natural and artificial ultraviolet (UV) radiation is provided. The method comprises: exposing a bioactive substance adapted to exhibit photochemical transformations that initiate vitamin D synthesis in nature to an UV radiation the vitamin-D synthesizing amount of which is to be determined; measuring change of absorbance of the bioactive substance upon exposition to the UV radiation; and correlating the measured change of the absorbance to a vitamin-D synthesizing amount, wherein the vitamin-D synthesizing amount corresponding to the measured change of the absorbance is the vitamin-D synthesizing amount corresponding to the UV radiation to which the bioactive substance has been exposed.

According to a second aspect, a personal biodosimeter for determination in situ of vitamin-D-synthetic dose of natural and/or artificial ultraviolet (UV) radiation is provided. The biodosimeter comprises: a UV source; a sensing unit comprising a bioactive substance embedded in a matrix structure, the sensing unit adapted to be irradiated by the UV source and/or natural and/or artificial UV radiation; a photodetector located downstream the sensing unit, the photodetector sensitive to UV radiation and adapted to detect an output of the sensing unit; and a processor connected with the photodetector and adapted to process the output of the photodetector, the output of the photodetector being indicative of a change in absorbance of the sensing unit upon UV irradiation from the UV source and/or natural and/or artificial UV radiation.

Further aspects of the present disclosure are provided in the written description, drawings and claims of the present application.

The biodosimeters, methods and systems herein described can be used in connection with applications wherein measurement and control of specific vitamin-D-synthetic biological activity of solar and artificial ultraviolet (UV) radiation or irradiation is desired.

In particular in several embodiments, the biodosimeter, methods and systems herein described allows detection of Vitamin D synthetic ability of UV radiation in an environment that can be considered as mimicking biological samples such as mammal skin and in particular human skin.

Accordingly, in several embodiments, the biodosimeters, methods and systems herein described can be used in connection with applications in medicine, ecology, balneology (therapeutic uses of various types of bathing and hydrotherapy), cosmetology, agriculture, epidemiology, and in day-to-day activity for measurement and control of specific vitamin-D-synthetic biological activity of solar and artificial ultraviolet (UV) radiation or irradiation (also known as anti-rachitic activity).

The details of one or more embodiments of the disclosure are set forth in the accompanying drawings and the description below. Other features, objects, and advantages will be apparent from the description and drawings, and from the claims.

BRIEF DESCRIPTION OF THE DRAWINGS

The accompanying drawings, which are incorporated into and constitute a part of this specification, illustrate one or more embodiments of the present disclosure and, together with the detailed description and examples sections, serve to explain the principles and implementations of the disclosure.

FIG. 4A shows absorbance change in porous silica films. FIG. 4B shows absorbance change in polymer films. FIG. 4C shows absorbance change in liquid crystal films. Previtamin D is photosynthesized in vitro in an ethanol solution.

DETAILED DESCRIPTION

Provided herein are a biodosimeter, methods and systems to detect UV absorption and/or vitamin D synthetic ability of UV radiation.

The terms "detect" or "detection" as used herein indicates the determination of the existence, presence or fact of a target (e.g. vitamin D) or a signal (e.g. UV radiation) in a limited portion of space, including but not limited to a sample, a reaction mixture, a molecular complex and a substrate. The detection can be quantitative or qualitative. A detection is "quantitative" when it refers, relates to, or involves the measurement of quantity or amount of the target or signal (also referred as quantitation), which includes but is not limited to any analysis designed to determine the amounts or proportions of the target or signal. A detection is "qualitative" when it refers, relates to, or involves identification of a quality or kind of the target or signal in terms of relative abundance to another target or signal, which is not quantified The term "vitamin D" as used herein indicates a group of fat-soluble prohormones, the two major forms of which are vitamin $D_2$ (or ergocalciferol) and vitamin $D_3$ (or cholecalciferol). Vitamin D is typically obtained in an organism from sun exposure, food, and supplements, is biologically inert and undergoes two hydroxylation reactions to be activated in the organism. For example, an active form of vitamin D typically found in mammals, and in particular humans, is calcitriol (1,25-Dihydroxycholecalciferol). The term vitamin D also refers to these metabolites and other analogues of these substances.

Among the principal chemical species of vitamin D, Vitamin $D_2$, or ergocalciferol ($C_{28}H_{44}O$) is typically formed from ergosterol (provitamin $D_2$) under ultraviolet irradiation in plants, while the synthesis of vitamin $D_3$, or cholecalciferol ($C_{27}H_{44}O$) typically occurs in mammal skin as a result of photochemical isomerization of 7-dehydrocholesterol (7-DHC, provitamin $D_3$).

An appropriate way to determine the vitamin-D-synthetic dose of solar/artificial UV radiation is that of using exactly the same photoprocesses that underlie the natural synthesis of vitamin D, namely, provitamin D photoisomerization upon ultraviolet irradiation, which forms the immediate precursor of vitamin D-previtamin D in accordance to the scheme:

where the arrows show individual photoconversions upon UV irradiation with UV quantum energy hv. In such way, the quantity of the photosynthesized previtamin D would be a natural biological measure of antirachitic UV biodose received.

However, determination of previtamin D concentration upon UV irradiation of initial Provitamin D is significantly affected by side photoconversions resulting in the formation of a multicomponent photoisomer mixture. That is why Webb et al. in their studies of seasonal changes of the vitamin-D-synthetic activity of sunlight by means of an in vitro model of vitamin D synthesis (ethanol solution of provitamin D3) used chromatographic analysis for determination of the concentration of accumulated previtamin D that eliminate possibility of UV biomonitoring in situ. See A. R. Webb, L. W. Kline, M. F. Holick, Influence of season and latitude on the cutaneous synthesis of vitamin of D3: exposure to winter sunlight in Boston and Edmonton will not promote vitamin of D3 of in human skin, J. Clin. Endocrinol. Metabol. Vol. 67 (1988) 373-378.

In accordance with the present disclosure, preference conditions to maximize only one of many possible ways of previtamin D photoconversion are provided, to allow unambiguous interpretation of the change of absorbance at a fixed wavelength and the received dose of bioactive (antirachitic) ultraviolet radiation in accordance with the equation $$\Delta A = A_t - A_0 \qquad (1)$$

where $A_t$ and $A_0$ are the absorbance values before and after an UV exposure.

According to embodiments of the present disclosure, molecules of provitamin D are inserted in a specially selected matrix, that significantly inhibits competitive ways of previtamin D photoconversions in favor of one desired way only. The matrix is selected to be resistant to UV radiation and transparent in the absorption band of provitamin D. The measurement of the received UV dose is carried out by registration of the absorbance change in a spectral range which corresponds to one of the absorption bands (~280 nm) in the provitamin D spectrum.

The specially selected matrix can be made of porous silicate, polymeric, liquid-crystal films, or a polymer dispersed liquid crystal (PDLC). The received UV dose is determined using a calibration chart that establishes a relationship between change in absorbance and such UV dose. According to some embodiments of the disclosure, such relationship is linear, with the slope depending on provitamin D concentration. According to other embodiments, the relationship can be parabolic or have a different shape.

Throughout the present disclosure, the term "photosensitive material" will be used from time to time to indicate the above films with an admixture of provitamin D.

In accordance with the present disclosure, in order to determine the physical UV doses ($J/m^2$) of any UV source from the absorbance change $\Delta A$ of the photosensitive material, a calibration curve is initially plotted using a preliminarily measured UV irradiance from a source with an UV radiometer in $W/m^2$. The proper physical dose may then be found from this plot according to the difference $\Delta A = A_t - A_0$.

Determination of antirachitic UV doses (concentrations of previtamin D) from the absorbance change is carried out with a calibration curve obtained by simultaneously exposing provitamin D in a film and in ethanol solution.

In some embodiments, methods systems and biodosimeter herein described can be used to detect UV absorption and related vitamin D synthesis in individual in need of vitamin D. As known, lack of vitamin $D_3$ causes rickets in children and osteoporosis in adults. Moreover, as revealed recently, many serious diseases of heart and internal organs may also be caused by the vitamin $D_3$ deficiency. With due regard to the above, monitoring of specific antirachitic biological activity of ultraviolet radiation, i.e. its vitamin-D-synthetic ability, is gained in importance, especially in view of current pandemy of vitamin D deficiency. See, e.g., Michael F. Holick, Vitamin D: A Millenium Perspective, J. Cell. Biochem., Vol. 88 (2003) 296-307.

EXAMPLES

The biodosimeter, methods and systems herein described are further illustrated in the following examples, which are provided by way of illustration and are not intended to be limiting.

In particular, exemplary biodosimeter, methods and systems herein described were developed following completion of a study performed by Applicants and concerning spectrophotometric approaches to determine UV absorption and radiations.

A spectrophotometric analysis was developed in I. Terenetskaya, Spectral monitoring of biologically active solar UVB radiation using an in vitro model of vitamin D synthesis, Talanta, Vol. 53 (2000)195-203, as also disclosed in Ukrainian Patent UA No 19525 Method of control of bioactive ultraviolet radiation by I. P. Terenetskaya and K. O. Terenetsky. In particular, a solution of 7-dehydrocholesterol in ethanol is exposed to UV radiation in a standard quartz spectrophotometric cuvette. The absorption spectra of the solution are registered with a spectrophotometer in the range of 230-330 nm before and after UV exposures. The spectra are further processed with a computer to determine the concentration of accumulated previtamin D, which is the measure of received antirachitic UV biodose.

Applicants have then examined possibility of a simplified method of UV absorption spectroscopy, similar to majority of chemical dosimeters, where the change in absorbance of a photosensitive material is measured before and after UV exposures at a particular wavelength, for example, at 280 nm, that corresponds to a maximum of absorption of 7-dehydrocholesterol. However, a preliminary analysis of experimental data showed that the presence of several competitive channels of previtamin D photoconversion substantially reduced reliability of estimate, because of ambiguity of connection between the absorbance change and received UV biodose. See Terenecka I. P., Teor. and eksper. chemistry, Vol. 44 (2008)279-283, and T. N. Orlova, I. P. Terenetskaya, Zhurn. Prikl. spektroskopii, Vol. 76 (2009)265-269.

In particular, in the above mentioned experiments it was noted that 1) under irradiation of provitamin D the initial accumulation of previtamin D is accompanied by an absorbance decline, however its subsequent transformation into tachysterol is accompanied by absorbance growth; 2) irreversible transformations of previtamin D into toxisterols result in absorbance decline to zero. Therefore, the nonmonotonic dependence of the absorbance on the exposure time observed in the above experiments, causes ambiguous dependence on the received UV doses and, thus, impairs the use of solution of 7-dehydrocholesterol in ethanol for UV dosimetry by measuring the absorbance at a fixed wavelength.

Applicants have addressed the above observations and provided a biodosimeter, methods and systems that are illustrated in the present disclosure and exemplified herein.

In the following examples illustrate exemplary methods and systems are based on detection of UV absorbance and UV radiation related vitamin D synthesis performed with specific materials and specific detection method. A person skilled in the art will appreciate the applicability of the features described in detail for the exemplified materials and methods to other methods and materials according to the present disclosure.

Example 1

UV Radiation Detection and Quantitative Detection of Related Synthesis of Vitamin D Plotting of absorbance changes vs a dose of UV irradiation using porous silica film with 7-dehydrocholesterol (7-DHC) as a photosensitive material.

Film Preparation

According to this example, mechanically stable UV transparent homogeneous porous silica films (glasses) with content of 7-DHC entrapped within a silica matrix were provided. Parameters such as temperature, solution pH, particular alkoxide precursor and solvent, and their relative concentrations, were initially determined to provide an optimum ratio of porosity, thickness and UV/VIS absorbance/transparency of the film. The pore size was optimized with regard to expected suppression of conformational mobility of 7-DHC (and its photoisomers) implied by their immobilization on the OH-groups of silica surface. Furthermore, the acidity regime of sol-gel process was balanced in view of known unfavorable acid effect on 7-DHC photochemistry.

Thick films are liable to be destroyed due to collapse of the primary particles at the stage of the film heat treatment, while in thin films the amount of immobilized 7-DHC is insufficient for accurate measurements of UV absorbance. Therefore, an adequate UV optical density (e.g., no less than 0.2) of the silica film with entrapped molecules 7-DHC (optimum film thickness and adequate amount of 7-DHC inside) should be designed.

According to this example, the following steps were followed for the preparation of the porous silica film: (1) under neutral pH, (2) the 7-DHC molecules were solubilized within β-cyclodextrin to protect the molecules against the interaction with silica OH-groups saving the conformation mobility, and (3) the solubilized molecules of 7-DHC were introduced within mesoporous silica films via adsorption to favor homogeneous distribution of 7-DHC.

The mesoporous silica films of this example were prepared by a sol-gel method using cationic surfactant cetyitrimethylammonium bromide (CTAB, Aldrich) as a template agent to provide homogeneous porosity. The precursor sol was prepared by hydrolysis of TEOS in a mixture of distilled water, ethanol (Fluka), and 1 M HCl solution. Twenty-four hours after hydrolysis, water solution of crAB was added to the solution.

The total molar ratios of the example was 1 TEOS:0.1 CTAB:0.02 HCl:10 H20:5 C2H5OH. The material was deposited onto clean quartz substrates by dip coating. The films were dried for 12 hours at ambient temperature, followed by heat treatment at 400° C. with a rate of 10 C/min and calcinated at 350° C. for 6 h. The parameters of low-level cell of silica film were as follows: pore diameter=2.84 nm, wall thickness=1.17 nm, surface Ssp=550 $m^2/g$.

X-ray diffraction (XRD) of the film demonstrated 3 signals: (2 theta): 2.7:25:8.6, corresponding to an interlaminar distance of 34.7 A. At 500° C. the distance was 30.4 A, and at 600° C. collapse of the porous structure occurred. Hence, the film was treated at 350° C. during the hour before the adsorption of 7-DHC.

Plotting

Figure 1A:
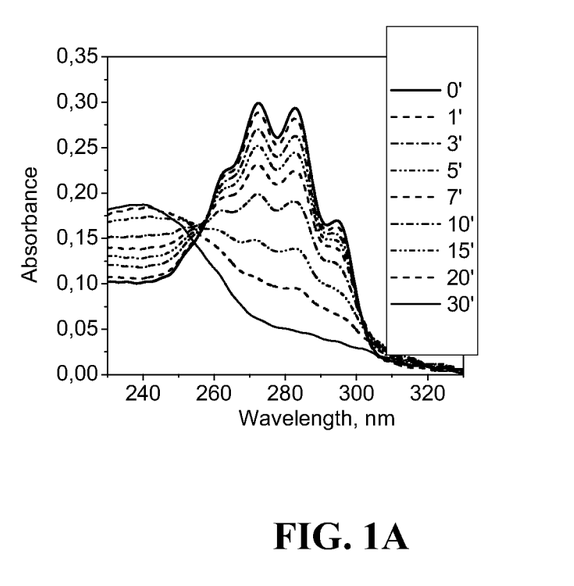
FIG. 1A shows the change in the absorption spectrum of provitamin D in a porous silica film as a result of UV irradiation with a fluorescent EL-30 lamp for 30 minutes.

The absorption spectrum of porous silica film with 7-DHC before UV irradiation recorded with a Perkin & Elmer Lambda 25 UV/VIS spectrophotometer in the range of 230-330 nm. A value of absorbance $A_0$ at 280 nm was determined. Then the film was exposed to UV radiation from a fluorescent EL-30 lamp for a series of exposures from 0 minutes to 30 minutes. After each of the exposures the absorption spectrum of the film was recorded and value of absorbance $A_t$ at 280 nm was determined, as shown in FIG. 1A. The power of UV irradiance provided by the EL-30 lamp at the film location was measured by the NIS calibrated spectrometer EPP2000C-UV+VIS manufactured by Stellarnet, Inc.

Figure 1B:
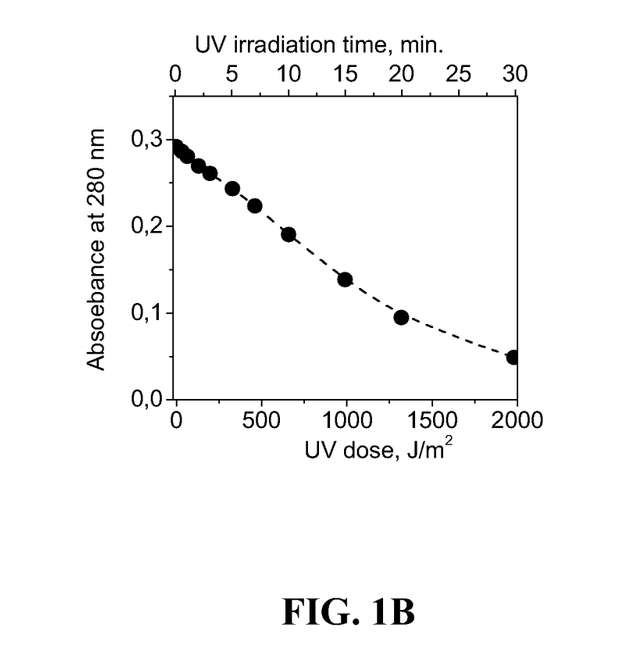
FIG. 1B shows the dependence of the absorbance measured at a 280 nm wavelength (vertical axis) on the received UV doses (horizontal axis).

A curve of absorbance change $\Delta A$ at 280 nm versus a UV dose was then plotted, as shown in FIG. 1B. Such curve can be used later for determination of the physical UV dose ($J/m^2$) corresponding to a change of absorbance $\Delta A = A_t - A_0$.

In order to determine the UV biodose, i) the porous silica film with the admixture of 7-DHC and ii) a cuvette with ethanol solution of 7-DHC where located at the same distance from the UV source and simultaneously exposed to the same. Absorption spectra of the film and of the solution in the range of 230-330 nm were recorded with a Perkin&Elmer Lambda 25 UV/VIS spectrophotometer before and after the fixed UV exposures.

Figure 4A:
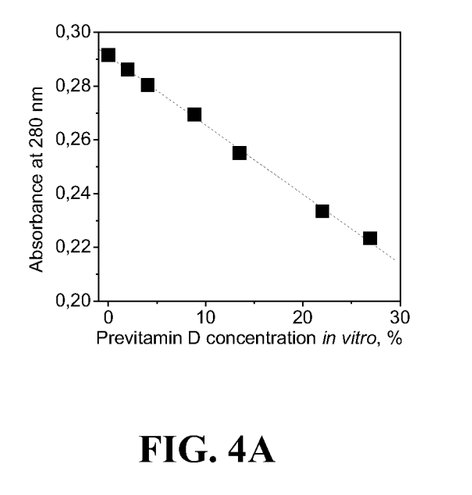
FIGS. 4A-4C show cross-correlation dependences between absorbance change (vertical axis) and previtamin D concentration (horizontal axis).

The solution spectra were computer processed to determine dependence of the concentration of previtamin D on the irradiation time. By correlating $\Delta A$ with the concentrations of previtamin D, measured with identical exposures, a calibration curve of absorbance dependence vs previtamin D concentration (biological UV doses) was plotted, as shown in FIG. 4A. Future biological UV doses can be determined from the change $\Delta A$ using the calibration curve of FIG. 4A.

Example 2

UV Radiation Detection and Quantitative Detection of Related Synthesis of Vitamin D Absorbance changes vs a dose of UV irradiation using polymer film with 7-dehydrocholesterol as photosensitive material were plotted.

Film Preparation

Applicants have examined various UV absorption spectra and noted that polyvinyl alcohol (PVA) polymer is more appropriate than polyvinyl butyl (PVB) and polysulphone (PS)-based films because their own absorption bands are in the same spectral range as 7-DHC. However, the different solubility of PVA and 7-DHC provides an obstacle to the development of preparation technology of UV transparent optically homogenous free (without quartz substrates) PVA film impregnated with UV sensitive biomolecules (7-DHC).

Since PVA is water-soluble and 7-DHC is fat-soluble, Applicants initially dissolved PVA (MW 60000) in water to obtain a 5% water solution of polyvinyl alcohol. An ethanol solution of 7-DHC was subsequently slowly introduced into the polymer solution (e.g., drop by drop), which was thoroughly mixed, put on the glass substrate and slowly evaporated. Films of larger diameter (e.g., 7.5 cm) were prepared in Petri's vessels. The films were then dryed in desiccators. The parameters were as follows: the concentration of the initial solution of PVA in water, the drying conditions, and the appropriate concentration of 7-DHC within the PVA-based film needed for the UV spectra registration. The obtained PVA films were mechanically stable, colorless and optically transparent.

UV irradiation of the samples was performed using a low pressure mercury lamp BUV-30 (Aicc=254 nm) and a luminescent lamp EL-30 (280-330 nm). Spectral irradiance of the UV lamps at a sample distance of 8 cm was determined using calibrated spectrometer EPP2000C-UV+VIS (StellarNet, Inc), and the following data were obtained: 0.3 $mW/cm^2$ for the BUV-30 lamp and 0.25 $mW/cm^2$ for the total spectral range 270-380 nm of the EI-30 lamp (0.11 mW/cm2 in the UVB spectral range).

The photoreaction course was followed by UV absorption spectroscopy, i.e. absorption spectra of the samples were recorded by a Perkin & Elmer Lambda 25 UV/VIS spectrophotometer within 230-330 nm before and after fixed UV exposures. An ethanol solution of 7-DHC was simultaneously irradiated in parallel under the same conditions.

Plotting

Figure 2A:
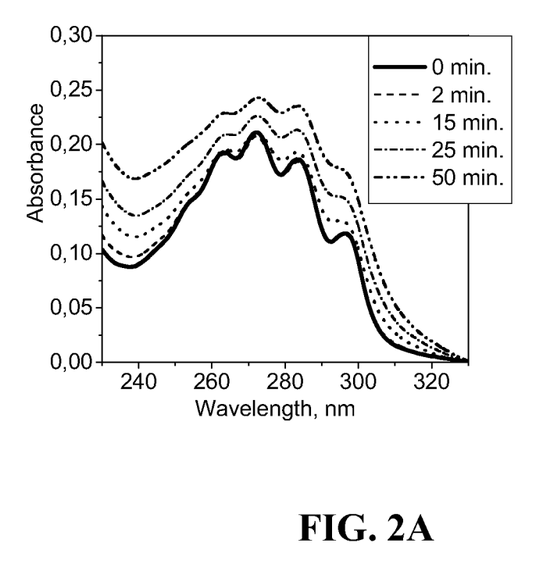
FIG. 2A shows the change in the absorption spectrum of provitamin D in a polymer film as a result of UV irradiation with fluorescent EL-30 lamp for 50 minutes.
Figure 2B:
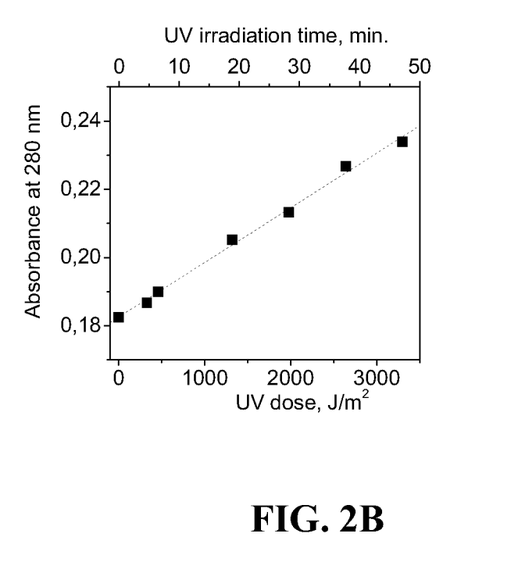
FIG. 2B shows the dependence of the absorbance measured at a 280 nm wavelength (vertical axis) on the received UV doses (horizontal axis).
Figure 4B:
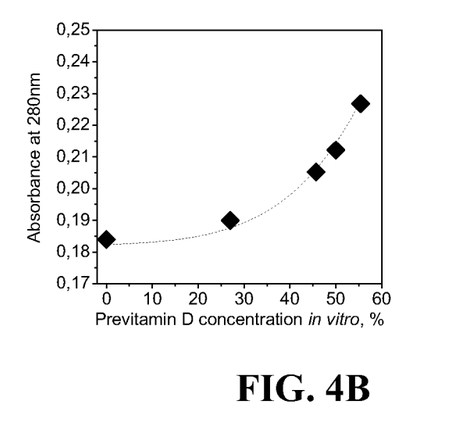

The steps described in Example 1 above were then repeated. The results are shown in FIGS. 2A, 2B, and 4B.

Example 3

Figure 3A:
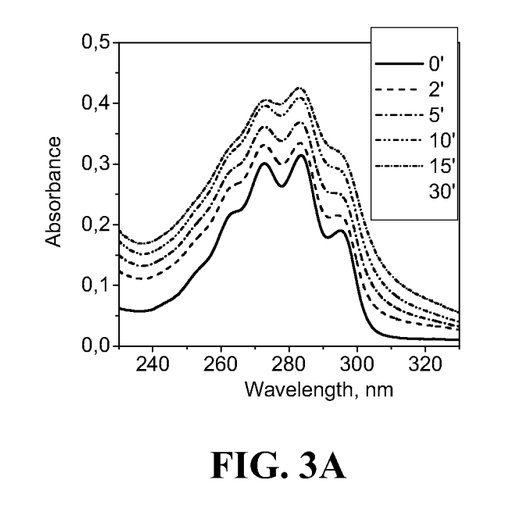
FIG. 3A shows the change in the absorption spectrum of provitamin D in a nematic liquid crystal (MLC-6815) as a result of UV irradiation with fluorescent EL-30 lamp for 30 minutes.
Figure 3B:
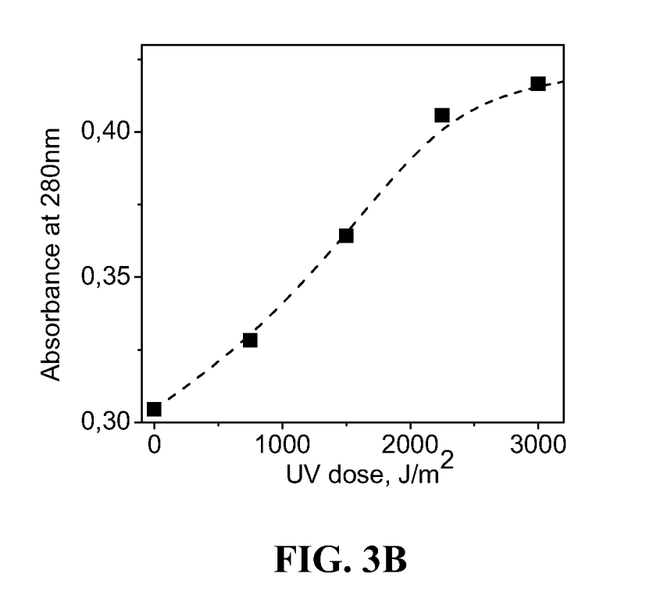
FIG. 3B shows the dependence of the absorbance measured at a 280 nm wavelength on the received UV doses (horizontal axis).
Figure 4C:
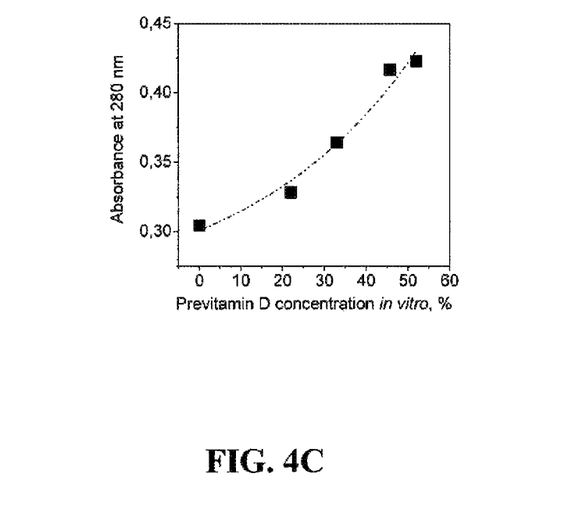

UV Radiation Detection and Quantitative Detection of Related Synthesis of Vitamin D Absorbance changes vs a dose of UV irradiation using a liquid crystalline film with 7-dehydrocholesterol as a photosensitive material were plotted. The steps described in Example 1 above were then repeated. The results are shown in FIGS. 3A, 3B, and 4C.

The method of determination of the vitamin-D-synthetic UV dose can find wide application in fields such as ecology, medicine, cosmetology, etc. Possible uses relate to i) everyday control of solar UV radiation capable to initiate the vitamin D synthesis;

ii) dosimetric control of artificial UV sources (lamps and lasers);

iii) personal control of antirachitic ultraviolet doses at epidemiologic researches;

iv) control of the received antirachitic dose of ultraviolet irradiation in the phototherapy clinics and solaria;

v) uses in zoology, biology, oceanology, agriculture, etc.

According to a further embodiment of the present disclosure, the above method is implemented in a personal biodosimeter.

Example 4

UV Biodosimeter

Figure 5:
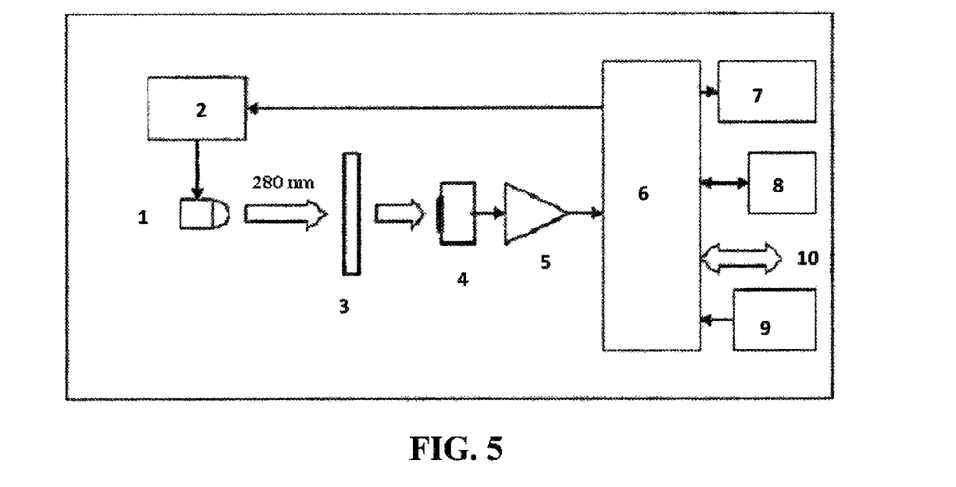
FIG. 5 shows a schematic diagram of a personal biodosimeter employing the method according to the present disclosure.

FIG. 5 shows a diagram of a personal biodosimeter according to an embodiment of the disclosure. The personal biodosimeter contains a light-emitting diode LED (1), which irradiates at 280 nm. LED (1) is connected to a power supply (2). A sensing unit containing a film with a photosensitive material (3) is also provided. The photosensitive material can be one of the materials described in the examples above. A photodiode (4) receives the output of the sensing unit (3). The output of the photodiode (4) is amplified by an amplifier (5) and then input to a microcontroller (6) containing an analog-to-digital converter (ADC). An LCD indicator panel (7), a keyboard panel (8), a chemical current source (9) and a USB communication port (10) are connected to the microcontroller (6). Means for transferring data over a telecommunications system, such as a cellular network, can also be provided.

During operation, one of the films with photosensitive material described above is placed into the sensing unit (3), and the power supply unit is turned on. As soon as this occurs, the indicator panel can prompt the user to choose a "measuring" mode of operation. In this mode of operation, microcontroller (6) starts operation of LED (1) through the power supply (2) in order to provide a stable luminous flux of UV radiation at the wavelength 280 nm. This radiation $I_f$ (light intensity) passes through a cell or slit containing the photosensitive material (3) (film with provitamin D) and is fed to photodiode (4). As a result, a signal proportional to the intensity of the UV radiation is formed at the output of photodiode (4). This signal is transmitted to the amplifier (5) to provide a voltage signal whose amplitude is sufficient for normal operation of the ADC of the microcontroller (6) in the total range of the UV radiation flux. By way of example, the ADC can transform analog voltage values into digital values ranging from 1 to 1024.

The digital value of $I_f$ obtained by the ADC can be written down into a separate memory cell. As soon as the signal coding process is completed, the microcontroller (6) can switch off the power supply (2) of LED (1). Moreover, the microcontroller (6), through a program saved in a memory section of the microcontroller (6), calculates the film absorbance $A_0$ by the formula $$A_0 = lg I_0 / I_f \qquad (2)$$

where $I_f$ is the light intensity which passed through the film and $I_0$ is the incident light intensity preliminarily measured without film.

After UV irradiation of the film, the same operations are repeated and $A_t$ is determined. Determination of $A_t$ allows determination of $\Delta A$ through the relationship $\Delta A = A_t - A_0$. At this point, the curve shown in FIGS. 1B, 2B, 3B can be used to determine the vitamin D synthetic UV biodose associated to $\Delta A$. Association between each value of $\Delta A$ and the vitamin D synthetic UV biodose can be contained in a data file previously stored in a memory of the microcontroller (6).

The amount of accumulated previtamin D can be determined from the dependence of $\Delta A$ on the concentration of previtamin D previously calculated through the curves of FIGS. 4A, 4B, 4C. Also in this case, association between each value of $\Delta A$ and the concentration of previtamin D can be contained in a data file previously stored in a memory of the microcontroller (6).

Moreover, in accordance with the embodiment of FIG. 5, measurement date and time are saved in memory together with the UV dose value. The following information can, for example, appear on the indicator panel (7): the date and time of the first measuring, the date and time of the last measuring and value of the received UV dose for this period.

Therefore, during operation, the biodosimeter can execute the following processing sequence:
1. Setting date and time.
2. Switching on LED (1) for a time sufficient to allow photodiode signal coding and measuring of $I_0$. Usually, this time is no more than 20 μs.
3. Measurement of $I_f$ which is the light intensity passed through the photosensitive material (3) (film with provitamin D).
4. Transformation of the information obtained into the received UV dose through calibration curve values.
5. Storage of the measured UV data
6. Representation of the measured UV dose at the LCD indicator panel (7)
7. Transfer of the stored data to a computer and/or a telecommunication system via USB communication port (10).

During calibration and/or maintenance, operations such as preliminary calibration work, periodical memory cleaning and software update can be conducted.

The person skilled in the art will understand that use of the UV LED (1) can affect the photosensitive material absorbance during the measuring procedure. Such problem is avoided by performing calculation during the measuring procedure. Optical radiation power of UV LED T9F28B is 500 μW, which amounts only to $1*10^{-8}$ J during a 20 μs measuring interval. The amount of film surface exposed to the UV rays during measuring procedure is ~10 mm², which gives a surface dose $1*10^{-7}$ J/cm². Such additional dose is 1000 times less than the measuring error of the device and can be therefore ignored.

In summary, in several embodiments a matrix with a biologically active substance is exposed to UV radiation. The biologically active substance is selected to initiate photoconversions originating vitamin D synthesis. An optical parameter of the biologically active substance is being changed under UV irradiation. Change of the optical parameter is measured, thus measuring the amount of UV radiation that has caused the vitamin D synthesis occurred through photoconversion. Measuring occurs by way of a dosimeter The examples set forth above are provided to give those of ordinary skill in the art a complete disclosure and description of how to make and use the embodiments of the methods and devices for in situ determination of a vitamin-D synthesizing amount of natural and artificial UV irradiation of the disclosure, and are not intended to limit the scope of what the inventors regard as their disclosure. Modifications of the above-described modes for carrying out the disclosure may be used by persons of skill in the art, and are intended to be within the scope of the following claims.

All patents and publications mentioned in the specification are indicative of the levels of skill of those skilled in the art to which the disclosure pertains. All references cited in this disclosure are incorporated by reference to the same extent as if each reference had been incorporated by reference in its entirety individually.

The entire disclosure of each document cited (including patents, patent applications, journal articles, abstracts, laboratory manuals, books, or other disclosures) in the Background, Summary, Detailed Description, and Examples is hereby incorporated herein by reference.

It is to be understood that the disclosures are not limited to particular compositions or biological systems, which can, of course, vary. It is also to be understood that the terminology used herein is for the purpose of describing particular embodiments only, and is not intended to be limiting. As used in this specification and the appended claims, the singular forms "a," "an," and "the" include plural referents unless the content clearly dictates otherwise. The term "plurality" includes two or more referents unless the content clearly dictates otherwise. Unless defined otherwise, all technical and scientific terms used herein have the same meaning as commonly understood by one of ordinary skill in the art to which the disclosure pertains.

Although any methods and materials similar or equivalent to those described herein can be used in the practice for testing of the products, methods and system of the present disclosure, exemplary appropriate materials and methods are described herein as examples and for guidance purpose.

A number of embodiments of the disclosure have been described. Nevertheless, it will be understood that various modifications may be made without departing from the spirit and scope of the present disclosure. Accordingly, other embodiments are within the scope of the following claims.

The invention claimed is:

1. A method for determination in situ of vitamin-D synthesizing amount of natural and artificial ultraviolet (UV) radiation, comprising:
   embedding a bioactive substance into a material adapted to inhibit competitive channels of intermediate photoproduct photoconversion
   exposing the bioactive substance adapted to exhibit photochemical transformations that initiate vitamin D synthesis in nature to an UV radiation the vitamin-D synthesizing amount of which is to be determined;
   measuring change of absorbance of the bioactive substance upon exposition to the UV radiation; and
   correlating the measured change of the absorbance to a vitamin-D synthesizing amount, wherein the vitamin-D synthesizing amount corresponding to the measured change of the absorbance is the vitamin-D synthesizing amount corresponding to the UV radiation to which the bioactive substance has been exposed.

2. The method according to claim 1, wherein the bioactive substance is provitamin D.

3. The method according to claim 2, wherein the provitamin D is ergosterol (provitamin D2).

4. The method according to claim 2, wherein the provitamin D is 7-dehydrocholesterol (provitamin D3).

5. The method according to claim 1, wherein the material is resistant to ultraviolet radiation and transparent in the spectral range of absorption of the bioactive substance.

6. The method according to claim 5, wherein the material is selected from the group consisting of a porous silica film, a polymer film, a liquid crystalline layer, and a polymer dispersed liquid crystal (PDLC).

7. The method according to claim 6, wherein the material is porous silica film entrapping the bioactive substance and wherein pore size of the porous silica film is optimized to suppress conformational mobility of the bioactive substance and photoisomers of the bioactive substance.

8. The method according to claim 7, wherein the bioactive substance is 7-DHC solubilized within 6-cyclodextrin introduced within the porous silica film via adsorption.

9. The method according to claim 6, wherein the polymer film is polyvinyl alcohol (PV
   A) polymer and wherein embedding occurs by:
      dissolving PVA in water to obtain a solution of polyvinyl alcohol;
      introducing an ethanol solution of the bioactive substance;
      mixing the solution of polyvinyl alcohol with the ethanol solution of the bioactive substance; and drying.

10. The method according to claim 1, wherein the absorbance is in the spectral region corresponding to the one of the absorption bands of the bioactive substance.

11. The method according to claim 10, wherein the absorption band is an absorption band with a maximum near to 280 nm.

12. The method according to claim 1, wherein the absorbance is absorbance A and wherein measuring the change $\Delta A$ occurs by measuring a difference change $\Delta A = A_t - A_o$ between absorbance $A_t$ upon exposition to UV radiation and absorbance $A_o$ prior to exposition to UV radiation.

13. The method of claim 1, wherein correlating the measured change of the absorbance parameter to a vitamin-D synthesizing amount occurs through comparison between a first calibration curve showing absorbance in function of UV radiation of the bioactive substance embedded in a material resistant to ultraviolet radiation and transparent in the spectral range of absorption of the bioactive substance and a second calibration curve showing synthesizing amount of the bioactive substance in function of time of the bioactive substance without said material and establishing, upon said comparison a curve showing said absorbance in function of said synthesizing amount.

14. A personal biodosimeter for determination in situ of vitamin-D-synthetic dose of natural and/or artificial ultraviolet (UV) radiation, comprising:
   a UV source;
   a sensing unit comprising a bioactive substance embedded in a matrix structure, the sensing unit adapted to be irradiated by the UV source and/or natural and/or artificial UV radiation, wherein the matrix is selected from the croup consisting of porous silica film, polymer film, polymer dispersed liquid crystal (PDLC), and a film containing the bioactive substance;
   a photodetector located downstream the sensing unit, the photodetector sensitive to UV radiation and adapted to detect an output of the sensing unit; and
   a processor connected with the photodetector and adapted to process the output of the photodetector, the output of the photodetector being indicative of a change in absorbance of the sensing unit upon UV irradiation from the UV source and/or natural and/or artificial UV radiation.

15. The personal biodosimeter of claim 14, further comprising an analog-to-digital converter to convert the output of the photodetector before processing by the processor.

16. The personal biodosimeter of claim 14, further comprising a display panel connected with the processor.

17. The biodosimeter according to claim 14, wherein the UV source irradiates in a narrow spectral range corresponding to an absorption band of the bioactive substance.

18. The biodosimeter according to claim 14, wherein the bioactive substance is provitamin D2 or D3.

19. The biodosimeter according to claim 14, wherein the UV source irradiates at a wavelength of about 280 nm.

20. The biodosimeter according to claim 14, wherein the matrix with bioactive substance is replaceable.

21. A personal biodosimeter for determination in situ of vitamin-D-synthetic dose of natural and/or artificial ultraviolet (UV) radiation, comprising:
   a UV source;
   a sensing unit comprising a bioactive substance embedded in a matrix structure, the sensing unit adapted to be irradiated by the UV source and/or natural and/or artificial UV radiation, wherein the matrix is a material creating preferential conditions for a single previtamin D photoconversion;
   a photodetector located downstream the sensing unit, the photodetector sensitive to UV radiation and adapted to detect an output of the sensing unit; and
   a processor connected with the photodetector and adapted to process the output of the photodetector, the output of the photodetector being indicative of a change in absorbance of the sensing unit upon UV irradiation from the UV source and/or natural and/or artificial UV radiation.

* * * * *